United States Patent
O'Reilly et al.

(10) Patent No.: US 6,626,122 B2
(45) Date of Patent: Sep. 30, 2003

(54) DEACTIVATABLE BIOCIDES IN BALLAST WATER

(75) Inventors: Kirk T. O'Reilly, El Sobrante, CA (US); Michael E. Moir, San Rafael, CA (US); Dennis J. O'Rear, Petaluma, CA (US); Mark R. Buetzow, Novato, CA (US); Brian V. Dorsch, Concord, CA (US)

(73) Assignee: Chevron U.S.A. Inc, San Ramon, CA (US)

( * ) Notice: Subject to any disclaimer, the term of this patent is extended or adjusted under 35 U.S.C. 154(b) by 0 days.

(21) Appl. No.: 09/982,701

(22) Filed: Oct. 18, 2001

(65) Prior Publication Data

US 2003/0121464 A1 Jul. 3, 2003

(51) Int. Cl.$^7$ ............................................. B63B 25/08
(52) U.S. Cl. ...................... 114/74 R; 114/125; 210/764
(58) Field of Search ............................ 114/125, 74 R; 210/755, 764

(56) References Cited

U.S. PATENT DOCUMENTS

| | | | |
|---|---|---|---|
| 3,839,008 A | | 10/1974 | Shema et al. |
| 3,879,513 A | | 4/1975 | Shema et al. |
| 3,965,264 A | * | 6/1976 | Redmore ..................... 514/80 |
| 4,020,200 A | * | 4/1977 | Groszek et al. .......... 106/18.28 |
| 4,086,066 A | | 4/1978 | McDermott |
| 4,185,094 A | * | 1/1980 | Crump ..................... 106/18.29 |
| 4,188,380 A | | 2/1980 | Oswald |
| 4,293,339 A | * | 10/1981 | Supcoe et al. ............ 106/18.29 |
| 4,539,071 A | | 9/1985 | Clifford et al. |
| 4,568,663 A | | 2/1986 | Mauldin |
| 4,853,140 A | | 8/1989 | Payne et al. |
| 4,867,757 A | | 9/1989 | Payne |
| 5,023,267 A | * | 6/1991 | Clarkson et al. ............. 514/372 |
| 5,055,325 A | | 10/1991 | Trivett |
| 5,128,050 A | * | 7/1992 | Gill ............................ 210/755 |
| 5,192,451 A | * | 3/1993 | Gill ............................ 210/755 |
| 5,256,423 A | * | 10/1993 | Egusa et al. ................. 424/616 |
| 5,385,896 A | * | 1/1995 | Bryan et al. ................. 514/129 |
| 5,416,210 A | | 5/1995 | Sherba et al. |
| 5,433,863 A | | 7/1995 | Braden et al. |
| 5,932,112 A | * | 8/1999 | Browning, Jr. ............. 210/750 |
| 6,053,121 A | * | 4/2000 | Tamashima et al. ........ 114/125 |
| 6,069,142 A | | 5/2000 | Gaffney et al. |
| 6,125,778 A | * | 10/2000 | Rodden ..................... 114/74 R |
| 6,221,262 B1 | * | 4/2001 | MacDonald et al. ........ 210/757 |
| 6,235,954 B1 | * | 5/2001 | Wu et al. .................... 585/260 |
| 6,284,793 B1 | * | 9/2001 | Fuchs et al. ................. 514/557 |
| 6,417,136 B2 | * | 7/2002 | Cheung et al. ............. 502/330 |

FOREIGN PATENT DOCUMENTS

| | | |
|---|---|---|
| EP | 0472311 A2 | 2/1992 |
| EP | 0609079 A1 | 8/1994 |
| EP | 0921184 A1 | 6/1999 |
| JP | 4322788 A | 11/1992 |
| WO | 00/20534 A1 | 4/2000 |
| WO | 01/60971 A2 | 8/2001 |
| WO | 02/072478 A2 | 9/2002 |

OTHER PUBLICATIONS

Bolch, C.J., et al., *Chemical and Physical Treatment Options to Kill Toxic Dinoflagellate Cysts in Ships' Ballast Water*, J. Marine Env. Engg., vol. 1, 1993, pp. 23–29, Gordon and Breach Science Publishers, US.

Carey, F.A., et al., *Advanced Organic Chemistry, Chapter 2: Reactions of Carbon Nucleophiles with Carbonyl Groups The Mannich Reaction*, $2^{nd}$ edition, 1983, pp. 59–62. Plenum Press, New York.

Carlton, J.T., et al., *Shipping Study: The Role of Shipping in the Introduction of Nonindigenous Aquatic Organisms to the Coastal Waters of the United States (other than the Great Lakes) and an Analysis of Control Options*, The National Sea Giant College Program/Connecticutt Sea Grant Project R/ES–6, Report No. CG–D–11–95, Apr. 1995, National Technical Information Service, Springfield, VA.

Cohen, A.N., *Ships' Ballast Water and the Introduction of Exotic Organisms into the San Francisco Estuary: Current Status of the Problem and Options for Management*, CAL-FED Category III Steering Committee, Oct., 1998, San Francisco Estuary Institute, Richmond, CA.

De Montellano, P.R., et al., *Self catalyzed Inactivation of Hepatic Cytochrome P–450 by Ethynyl*, The Journal of Biological Chemistry, vol. 255, No. 12, Jun. 25, 1980, pp. 5578–5585, American Society for Biochemistry and Molecular Biology, Baltimore, MD.

De Montellano, P.R., *Alkenes, and Alkynes, Bioactivation of Foreign Compounds*, Chapter 5, 1985, pp. 121–155, Academic Press, Inc., New York.

*Global spread of microorganisms by ships*, Brief Communications, Nature, Nov. 2, 2000.

*Glutaraldehyde: The Right Biocide for Many Environments*, Union Carbide Corporation, 1999 Published by Union Carbide, Danbury CT.

(List continued on next page.)

Primary Examiner—S. Joseph Morano
Assistant Examiner—Lars A. Olson
(74) Attorney, Agent, or Firm—Burns, Doane, Swecker & Mathis, LLP

(57) ABSTRACT

The present invention relates to the use of deactivatable biocides in ballast water aboard a vessel. The present invention relates to methods of limiting the transfer of one or more life forms via ballast water comprising mixing an effective amount of the deactivatable biocide with the ballast water and irreversibly deactivating the deactivatable biocides before or upon discharge of the ballast water.

27 Claims, No Drawings

OTHER PUBLICATIONS

Grab, L.A., et al., *Comparative Biocidal Efficacy vs. Sulfate–Reducing Bacteria, Materials Performance*, vol. 32, No. 6, 1993, pp. 59–62, National Association of Corrosion Engineers, Houston, TX.

Hudgins, C.M., Jr., *Chemical Treatments and Usage in Offshore Oil and Gas Production Systems, Journal of Petroleum Technology*, vol. 44, No. 5, May 1992, pp. 604–611, Society of Petroleum Engineers, Richardon, TX.

Hyman, M.R., et al., *Acetylene Inhibition of Metalloenzymes, Analytical Biochemistry*, vol. 173, No. 2, 1988, pp. 207–220, Academic Press, Inc., New York.

Leung, Hon–Wing, *Ecotoxicology of Glutaraldehyde: Review of Envionmental Fate and Effects Studies, Ecotoxicology and Environmental Safety*, 49, 26–39, 2001, Section B, pp 26–39, Academic Press.

*Methods for Measuring the Acute Toxicity of Effluents and Receiving Waters to Freshwater and Marine Organisms*, $4^{th}$ Edition, EPA/600/4–90/027F, Aug. 1993, United States Environmental Protection Agency, Reproduced by: National Technical Information Service, U.S. Dept. of Commerce, Springfield, VA.

Morrison, R.T., et al., *Organic Chemistry*, $2^{nd}$ edition, 1966, pp. 631–632, Allyn and Bacon, Inc., Boston.

Roets, Piet, et al., *Stability and Handling of SASOL Semi-–Synthetic Jet Fuel, $6^{th}$ International Conference on Stability and Handling of Liquid Fuels*, Vancouver, B.C., Canada, Oct. 13–17, 1997, pp 789–804, Publisher National Technical Information Services, Springfield, Virginia.

Prior, S.D., et al., *Acetylene as a suicide substrate and active site probe for methane monooxygenase from Methylococcus capsulatus (Bath), Federation of European Microbiological Societies: Microbiology Letters*, vol. 29, 1985, pp. 105–109, Elsevier/North Holland, Amsterdam.

Stirling, D.I., et al., *Effect of Metal–Binding Agents and Other Compounds on Methane Oxidation by Two Strains of Methyloccoccus capsulatus, Archives of Microbiology*, vol. 114, 1977, pp. 71–76, Springer–Verlag.

Yeager, C.M., et al., *Inactivation of Toluene 2–Monooxygenase in Burkholderia cepacia G4 by Alkynes, Applied & Envionmental Microbiology*, vol. 65, No. 2, Feb. 1999, pp. 632–639, American Society for Microbiology.

U.S. patent application Ser. No. 09/982,714, O'Reilly, et al., *Inhibition of Biological Degradation in Fischer–Tropsch Products*, Filed on Oct. 18, 2001.

U.S. patent application Ser. No. 09/982,702, O'Reilly, et al., *Process for Disposing Biocide–Containing Cooling Water*, Filed on Oct 18, 2001.

U.S. patent application Ser. No. 09/982,699, O'Reilly, et al., *Deactivatable Biocides for Hydrocarbonaceous Products*, Filed on Oct. 18, 2001.

United Kingdom Search Report dated Apr. 9, 2003.

* cited by examiner

US 6,626,122 B2

DEACTIVATABLE BIOCIDES IN BALLAST WATER

FIELD OF THE INVENTION

The present invention relates to methods for using deactivatable biocides in ballast water used on ships and other vessels.

BACKGROUND OF THE INVENTION

Ballast water is used on ships in order to maintain appropriate ship draft, trim, stability, immersion, and hull integrity. Ballast water may be taken on in special ballast tanks or may be taken on in the cargo tanks of a ship. Ships travel with ballast water when carrying no cargo or light cargo and travel with little or no ballast on board when carrying a maximum cargo. The quantity of ballast water used in a ship can be quite large. For example, a 300,000 metric ton crude tanker has a ballast water capacity of 100,000 metric tons. Typically, the ratio of ballast water to ship capacity is 1:3 to 1:2.

Ballast water is normally taken on in one coastal region and is discharged in another coastal region. For example, ships take on ballast water from one port, travel to a second port, and discharge a large amount of ballast water in order to take on cargo at the second port. The discharge of ballast water has led to the introduction of non-native life forms in many areas, as the life forms from one coastal region to another vary. Even ships reporting no ballast on board may act as vectors for non-native life forms because the ballast tanks of such ships contain an unpumpable amount of residual ballast water.

One proposed method of limiting the introduction of foreign organisms into marine environments is for ships to discharge their ballast water in the open ocean prior to entering port. However, as mentioned above, ballast water is typically needed to maintain essential operating conditions of a ship, and it may be dangerous to discharge ballast water before reaching a port.

Another method for limiting the introduction of life forms in ballast water is to exchange near-coast ballast water for mid-ocean ballast water. Presumably, the life forms taken on board the ship in a near-coast environment are flushed into the mid-ocean. It is important that the ship maintain stability, draft, and other operating parameters during this exchange, and only ships that are designed for this practice can safely exchange ballast water. Ships may be retrofitted to permit this exchange, but such retrofitting is very expensive. Currently only a small proportion of the world's cargo fleet is capable of ballast water exchange. Ballast water exchange may be completed by (1) emptying the ballast tanks and refilling them one at a time, or (2) pumping three volumes of ocean water into the tanks to flush them. Neither approach is completely effective in eliminating foreign life forms. The first method leaves a heal in the tank which can harbor life forms, and the second method allows life forms to be retained during the mixing. The effectiveness of ballast water exchange has been estimated at 90% and usually takes about 2 days to safely complete.

Because the above methods are not as effective or efficient as ideally desired, other methods of controlling the transfer of life forms have also been proposed. One of these methods is the use of biocides. However, when biocides are used to kill life forms in ballast water, the ballast water may be toxic to indigenous life forms when discharged into the environment. By way of example, chlorine has been used as a biocide, but the discharge of the ballast water treated with chlorine has been prohibited in some areas as a chlorinated waste.

Accordingly, there is a need in the art for a method of limiting the transfer of life forms via ballast water that is effective and efficient, can be used on existing vessels, and has reduced environmental toxicity compared to traditional use of biocides.

SUMMARY OF THE INVENTION

The invention relates to the use of deactivatable biocides in ballast water. Deactivatable biocides can be used with ballast water on a ship to limit or prevent the introduction of one or more life forms from one environment into another environment where the ballast water will be discharged. The deactivatable biocides can be irreversibly deactivated before or upon discharge of the ballast water to minimize potential environmental damage.

One aspect of the present invention is a method of disposing of ballast water containing a deactivatable biocide. A vessel is provided that has ballast water from a first location. The ballast water contains an effective amount of deactivatable biocide. An effective amount of a neutralizing agent is added to the ballast water to deactivate the biocide. The ballast water is then discharged from the vessel at a second location.

Another aspect of the present invention is a method of inhibiting growth and reproduction of microorganisms in a ballast water system of a vessel. Ballast water is provided to the ballast water system from a first natural environment. An effective amount of a deactivatable biocide is added to the ballast water. The deactivatable biocide can be irreversibly deactivated before or upon disposal of the ballast water.

An additional aspect of the present invention is a method of limiting the transfer of one or more life forms from a first location to a second location via ballast water. A vessel having a ballast water tank is provided. Ballast water from the first location and an effective amount of a deactivatable biocide are mixed in the ballast water tank. An effective amount of a neutralizing agent is added to the ballast water to deactivate the biocide. At least a portion of the ballast water is then discharged at the second location.

A further aspect of the present invention is a method of limiting the transfer of one or more life forms from one location to another location via ballast water using Fischer-Tropsch derived deactivatable biocides. A vessel having a ballast water tank and a cargo tank is provided. Fischer-Tropsch-derived liquid products and a Fischer-Tropsch derived deactivatable biocide are synthesized from a Fischer-Tropsch synthesis process. One or more of the Fischer-Tropsch-derived liquid products are added to the cargo tank at a first location. The Fischer-Tropsch derived deactivatable biocide is added (at the first location) to the ballast water tank and/or to a biocide storage area on the vessel. The Fischer-Tropsch-derived liquid product or products in the cargo tank are then delivered to a second location. Ballast water from the second location and an effective amount of the deactivatable biocide are mixed in the ballast water tank. An effective amount of a neutralizing agent is added to the ballast water to deactivate the biocide. At least a portion of the ballast water is then discharged at the first location or a third location.

Yet another aspect of the present invention is a method of limiting the transfer of one or more life forms from a beginning location to a final location via ballast water using a deactivatable biocide and ballast water exchange. A vessel having a ballast water tank is provided and water from the beginning location is added to the ballast water tank. A portion of the ballast water is discharged at an intermediate location, and an effective amount of a deactivatable biocide is added to the remainder of the water from the beginning location. Water from the intermediate location is added to the ballast water tank. An effective amount of a neutralizing agent is added to the ballast water to deactivate the biocide, and at least a portion of the ballast water is discharged at the final location.

Definitions

Unless otherwise stated, the following terms used in the specification and claims have the meanings given below:

"Biocide" means any substance that kills or inhibits the growth of microorganisms, such as, for example, bacteria, molds, slimes, fungi, and the like.

"Branching index" means a numerical index for measuring the average number of side chains attached to a main chain of a compound. For example, a compound that has a branching index of five means a compound having a straight main chain with an average of approximately five side chains attached thereto.

"Syngas" is a mixture that includes hydrogen and carbon monoxide. In addition to these species, others may also be present, including, for example, water, carbon dioxide, unconverted light hydrocarbon feedstock, and various impurities.

"Deactivatable biocide" means any biocide that can be deactivated or neutralized once the danger of microbial growth has ended. Deactivated or neutralized means that the biocide is no longer capable of killing or inhibiting the growth of microorganisms to any significant degree. Therefore, a deactivated biocide may be released into the environment with significantly reduced environmental risk. According to the present invention, the deactivatable biocide is irreversibly deactivated, i.e. the deactivatable biocide does not re-generate to become active upon release to the environment.

"Fischer-Tropsch-derived deactivatable biocide" means a deactivatable biocide that may be generated as one of the many potential products of the Fischer-Tropsch synthesis process or may be generated as a component of the wastewater of the Fischer-Tropsch process. Fischer-Tropsch-derived biocides include, for example alkynes, oxygenates, and the like, and mixtures thereof.

"Fischer-Tropsch-derived liquid products" mean hydrocarbonaceous, liquid products derived from a Fischer-Tropsch process. Fischer-Tropsch-derived liquid products include, for example, Fischer-Tropsch naphtha, Fischer-Tropsch jet fuel, Fischer-Tropsch diesel fuel, Fischer-Tropsch solvent, Fischer-Tropsch lube base stock, Fischer-Tropsch lube base oil, Fischer-Tropsch lube base stock feedstock, and mixtures thereof.

"Heavy Fischer Tropsch product" means a product derived from a Fischer Tropsch process that boils above the range of commonly sold distillate fuels: naphtha, jet or diesel fuel. This means greater than 400° F., preferably greater than 550° F., and most preferably greater than 700° F. This stream may be converted to olefins by a thermal cracking process.

"Light Fischer Tropsch product" includes hydrocarbons boiling below about 700° F. (e.g., tail gases through middle distillates). It is largely in the $C_5$ to $C_{20}$ range with decreasing amount up to about $C_{30}$. The light product comprises paraffinic products with a significant portion of alcohols and olefins. In some cases the light product may comprise as much as 50%, and even higher, alcohols and olefins.

"Hydrocarbonaceous" means containing hydrogen and carbon atoms and potentially also containing heteroatoms, such as oxygen, sulfur, nitrogen, and the like.

"Hydrocarbonaceous Product" means any hydrocarbonaceous product, including both conventional hydrocarbonaceous products and those identified as rapidly biodegradable hydrocarbonaceous products. Hydrocarbonaceous products contain hydrogen and carbon atoms and may also contain heteroatoms, such as oxygen, sulfur, nitrogen, and the like. Conventional hydrocarbonaceous products include conventional petroleum products, for example, petroleum, diesel fuel, solvent, jet fuel, naphtha, lube base stock, lube base stock feedstock, and lube base oil.

"Rapidly Biodegradable Hydrocarbonaceous Product" means a hydrocarbonaceous product in which visual growth of microorganisms occurs in approximately ten days or less. Rapidly biodegradable hydrocarbonaceous products may include, for example, Fischer-Tropsch-derived liquid products; low aromatics diesel fuel; products derived from petroleum, diesel fuel, solvent, jet fuel, naphtha, lube base stock, lube base oil, lube base stock feedstock, synthetic crude; and mixtures thereof. Rapidly biodegradable hydrocarbonaceous products of the present invention preferably are Fischer-Tropsch-derived liquid products.

"Neutralizing Agent" means any compounds or reaction conditions that may be used to react a deactivatable biocide or to complex a deactivatable biocide to destroy the biocide's antimicrobial activity. A neutralizing agent effectively deactivates a biocide, thus neutralizing the biocide's antimicrobial effectiveness. According to the present invention, the neutralizing agent irreversibly deactivates the deactivatable biocide, i.e. the deactivatable biocide does not re-generate to become active upon release to the environment. Neutralizing agents may include, for example, nitrogen containing compounds, oxidation conditions, hydrogenation conditions, and the like.

"Oxygenates" mean hydrocarbon compounds containing oxygen, including, for example, alcohols, carboxylic acids, aldehydes, and the like.

"Paraffin" means any saturated hydrocarbon compound, i.e., an alkane with a chemical formula of $C_nH_{2n+2}$.

"Environment" or "natural environment" means any natural surroundings, including rivers, lakes, streams, oceans, underground aquifers and the like.

"Life form" means any living organism including viruses, bacteria, molds, fungi, algae, plants, animals, etc.

"Cargo" means any object or substance transported on ships which contain ballast tanks, including raw materials such as crude oil, ores, scrap metal, and lumber; manufactured goods such as refined petroleum products, automobiles, trucks, and furniture; and items for disposal such as garbage, municipal wastes, sewage sludges, and spent tires. Crude oils to be transported include synthetic crude oils such as produced by a Gas To Liquids process (e.g., a Fischer Tropsch process). Refined petroleum products to be transported include products that are refined from a syncrude produced by a Gas to Liquids process.

DETAILED DESCRIPTION OF ILLUSTRATIVE EMBODIMENTS

The present invention relates to the use of deactivatable biocides in ballast water. Many ships and vessels contain ballast water systems (i.e., ballast tanks, pumps, etc.) that are necessary for the correct operation of the ship. Deactivatable biocides can be used with ballast water on a ship to limit or prevent the introduction of one or more life forms from one environment into another environment where the ballast water will be discharged. A deactivatable biocide is added to or mixed with ballast water from a first location before discharging the ballast water at a second location. To avoid environmental concerns, the biocides of the present invention are ones that can be irreversibly deactivated before or upon disposal of the ballast water.

The effective amount of biocide to be added to or mixed with the ballast water preferably is an amount effective to prevent visible growth of microorganisms for at least one day, preferably at least two days, more preferably at least five days, and most preferably at least 10 days under ambient conditions when exposed to a certified inoculant. Alternatively, an effective amount of biocide is an amount effective to kill a predetermined life form in an amount of at least 50%, preferably at least 75%, and most preferably at least 90% within 96 hours.

In the first test, a certified inoculant consists of a source of bacteria initially isolated at ambient conditions using a rapidly biodegradable hydrocarbonaceous product as the sole source of carbon and energy, and that has been shown to grow on the hydrocarbanaceous product through two or more successive inoculations. Visual growth or formation of microorganisms may be measured quantitatively by measuring turbidity of the product in question. Turbidity is generally measured by using a turbidity meter, for example, a Hach Co. Model 2100 P Turbidimeter. A turbidity meter is a nephelometer that consists of a light source that illuminates a water/oil sample and a photoelectric cell that measures the intensity of light scattered at a 90° angle by the particles in the sample. A transmitted light detector also receives light that passes through the sample. The signal output (units in nephelometric turbidity units or NTUs) of the turbidimeter is a ratio of the two detectors. Meters can measure turbidity over a wide range from 0 to 1000 NTUs. The instrument must meet US-EPA design criteria as specified in US-EPA method 180.1.

By way of example, typical lube base oils measured at 75° F. have ranges of from 0 to 20 NTUs. Commercial Poly Alpha Olefins (PAOs) tend to have NTUs between 0 and 1. The visual formation of microorganisms is said to occur when the NTU value increases by two units from measurements made before and after microorganisms or inoculant are introduced into the sample. Measurements are made on the ballast water. Therefore, after treatment with an effective amount of deactivatable biocide the NTU value of the ballast water will not show an increase of two or more units in approximately ten days or less after introduction of an inoculant. According to the invention, the effective amount of deactivatable biocide added to the ballast water is at least 1 ppm biocide, preferably at least 10 ppm biocide, and more preferably at least 100 ppm biocide.

As mentioned above, the second test for measuring an effective amount of biocide to be added to the ballast water is an amount effective to kill a predetermined life form in an amount of at least 50%, preferably at least 75%, and most preferably at least 90% within 96 hours. The predetermined life form is a life form that is non-native to an environment where ballast water will be discharged. It is undesirable to introduce non-indigenous life forms into an environment via the discharge of ballast water because some non-native life forms may damage the ecology of such an environment if introduced therein. Examples of life forms that are particularly undesirable in areas where they are not native include cholera bacteria, dinoflagellates, and zebra mussels. As one of skill in the art would recognize, the amount of biocide needed to reach a given kill rate will not be the same for all life forms that may be present in the ballast water. In cases where it is desirable to kill more than one life form, the amount of biocide must be adjusted to kill the desired amount of the most resistant life form. By way of example, the effective amount of deactivatable biocide added to the ballast water is at least 0.1 ppm, preferably at least 2.0 ppm, and more preferably at least 5.0 ppm.

As one of skill in the art would readily understand and be able to devise, mixing of the biocide and the ballast water can be accomplished in a variety of ways. By way of example, the biocide and the ballast water may be mixed and then pumped into the ballast tanks. The biocide may be added to a ballast tank and then the ballast water may be added. In addition, the ballast water may be pumped into a ballast tank and then the biocide may be added. A method of mixing the ballast water and biocide may be selected in view of the biocide and the ballast water system.

Use of the deactivatable biocides in ballast water according to the present invention eliminates the disposal problems that accompany traditional use of biocides. According to the present invention, before the ballast water containing a deactivatable biocide is disposed, the deactivatable biocide is irreversibly deactivated or neutralized by addition of a neutralizing agent. After the deactivatable biocide is irreversibly deactivated or neutralized, the ballast water may be disposed of by directly releasing the water into the environment without further treatment or fear of environmental damage. Deactivation of the biocide minimizes environmental damage when the ballast water is introduced into the environment. Deactivation, according the present invention, is an irreversible process, i.e., the process may not be reversed re-generating the active biocide.

According to the present invention, the biocides are deactivatable biocides to avoid environmental concerns. Deactivatable biocides of the invention include aldehydes, alkynes, and the like. Deactivatable biocides of the invention that are aldehydes include, for example, glutaraldehyde, and deactivatable biocides of the invention that are alkynes include, for example, 1-hexyne and propargyl alcohol.

By way of example, aldehydes are a preferred deactivatable biocide of the invention. While not being limited by theory, it is believed that aldehydes, including, for example, glutaraldehyde, act to inhibit growth of microorganisms by a mechanism similar to the Mannich reaction. By this mechanism, aldehydes, including, for example, glutaraldehyde, form complexes with non-hindered amines. These non-hindered amines include primary amines, ammonia, ammonium ions, or combinations thereof. In biological systems, these non-hindered amines may be amino acids. Cell walls of living organisms contain amino acids (non-hindered amines) that may provide a reactive site for aldehydes to react. Aldehydes may form cross-linking complexes with the amino acids on the cell surface, disrupting cellular function and killing the cells.

In particular, glutaraldehyde may be a preferred deactivatable biocide. Glutaraldehyde has rapid efficacy against a broad spectrum of microorganisms. Furthermore, glutaraldehyde is easily and uniformly diluted without the need for stabilizers or heavy metals. Glutaraldehyde is nonionic and thus is compatible with other chemicals. Glutaraldehyde also tolerates salts and hard water conditions. A further advantage of glutaraldehyde is that it may be irreversibly deactivated.

By way of example, alkynes (compounds with carbon-carbon triple bonds, C/C) are another preferred deactivatable biocide of the invention. While not being limited by theory, it is believed that alkynes may act to irreversibly inhibit alkane oxidizing enzymes, including, for example, mono-oxygenase enzymes. Without alkane mono-oxygenase activity, microorganisms cannot survive. Primary alkynes have been shown to irreversibly inhibit alkane oxidizing enzymes, while secondary alkynes, R—C/C—R, may be more effective on aromatic monooxygenases.

Alkynes may behave as "suicide substrates," and as such, activity of the oxidizing enzymes initiates the alkynes' inhibitory processes. The enzymes attempt to act on the alkynes, and this action causes irreversible binding of the alkynes to the active site of the enzyme. Binding of alkynes to the enzyme's active site inhibits the enzymes from causing further oxidation. Benefits of using alkynes as biocides in the present invention include their low inherent toxicity and their ability to be irreversibly deactivated.

By way of example, the alkynes used as biocides of the present invention may include, but are not limited to, 1-hexyne (HC—C≡$C_4H_9$), propargyl alcohol (HC—C≡$CH_2OH$), and the like.

According to the present invention, the deactivatable biocides may be irreversibly deactivated by (a) reacting the biocide with a neutralizing agent to provide an inert or deactivated form of the biocide; or (b) complexing the biocide with a neutralizing agent to form a less toxic compound. As one of skill in the art will understand, the specific details of deactivation will depend on the particular deactivatable biocide used. The compounds, added in (a) to react with the biocide or in (b) to complex the biocide, are herein known as "neutralizing agents." The neutralizing agent according to the invention may be a compound, a series of compounds, or reaction conditions. According to the invention, the neutralizing agent may refer to compound (s) added to the biocide to irreversibly deactivate it or may refer to reaction conditions used to irreversibly deactivate the biocide. The neutralizing agents of the invention effectively and irreversibly deactivate the biocide. Deactivating the biocide means that the biocide no longer exhibits any significant degree of antimicrobial effects. Thus, the biocide may be released into the environment without affecting the growth of microorganisms or higher life forms. Furthermore, deactivation of the biocide is an irreversible process, i.e. the process may not be reversed re-generating the active biocide after it has been released into the environment.

By way of example, a deactivatable biocide of the present invention may be deactivated by reacting it with a neutralizing agent to provide an inert form. These reactions include, for example, oxidation and reduction. Oxidation can be accomplished by, for example, hydrogen peroxide, other organic peroxides, or an oxygenated halogen (for example, bleaches such as NaClO or $Ca(ClO)_2$). Oxidation is an effective means to deactivate virtually any type of biocide. Although oxidation may be an effective, convenient means of deactivating the biocide, use of halogenated oxidants may create the risk of introducing halogens into the ballast water and thus into the environment upon disposal (i.e., discharge) of the ballast water. As one of skill in the art would understand, biocides and subsequent oxidants may be used in the present invention; however, it is important to choose the biocide and subsequent oxidant carefully. The oxidant should be selected such that it does not introduce unwanted by-products into the ballast water and thus into the environment upon disposal of the ballast water.

According to the invention, reduction of the biocide may also be an effective way to deactivate a biocide. By way of example, reduction of the biocide may be accomplished by hydrogenation. Hydrogenation may be an effective way to deactivate a biocide contained in ballast water. The process of hydrogenation is well known to those of skill in the art. Hydrogenation is performed using hydrogen gas. Typical catalysts for hydrogenation contain a Group VIII metal, such as platinum and palladium.

Complexing a biocide with a neutralizing agent may be used to form a less toxic compound and thus deactivate the biocide. The neutralizing agent is irreversibly complexed to the biocide to provide a compound that may be safely released into the environment. In determining neutralizing agents to complex with deactivatable biocides of the invention, the chemistry of the biocide's action to inhibit growth may be important.

By way of example, alkyne biocides may be effectively deactivated by hydrogenation. As a further example, to prevent aldehydes from attacking amino acids in the environment, aldehyde biocides, including, for example, glutaraldehyde, may be deactivated by irreversibly complexing or reacting them with nitrogen-containing compounds or oxygen scavengers. The nitrogen-containing compounds include, but are not limited to, primary amines, secondary amines, ammonia, amino alcohols, mixtures thereof, and the like. For example, glutaraldehyde may be deactivated by nitrogen-containing compounds including, for example, monoethanolamine, diethanolamine, methyldiethanolamine, diethylamine, aniline, and the like, and mixtures thereof.

Alkyne biocides such as propargyl alcohol may be neutralized by reacting the biocide with aqueous ammonia in the presence of copper (I) chlorides in order to precipitate the alkynes as a Cu salt. Silver chloride and mercuric chloride may also be used to precipitate an alkyne biocide. These agents may be supported on a solid bed of adsorbent and used to bind the biocide, thus removing the biocide from the ballast water.

Alkyne biocides may also be neutralized by reacting the biocide with aqueous acids to convert the alkynes to ketones, which are less toxic. It may also be possible to use strongly acidic ion exchange resins to convert alkynes to alcohols and ketones.

An effective amount of neutralizing agent of the present invention is the amount that effectively deactivates or neutralizes the biocide rendering it virtually harmless to the environment and rendering it ineffectual to inhibit microbial growth. When an effective amount of neutralizing agent is used, the water containing the deactivated biocide may be safely released into the environment. An effective amount of neutralizing agent to biocide is approximately 1 mole of neutralizing agent per mole of biocide. If excess neutralizing agent is used, the neutralizing agent may act as a biocide because it may be somewhat toxic. If much less neutralizing agent is added, it may not effectively deactivate or neutralize the biocide.

When the ballast water containing deactivatable biocide is to be neutralized, it is often important to measure the amount of biocide remaining in the ballast water. The amount of deactivatable biocide to be neutralized may be different than the initial amount added to the ballast water, as some of the biocide may have been lost or consumed. There are several ways to measure the deactivatable biocides in the ballast water, including, for example, gas chromatography, wet chemical test, mass spectroscopy, and other appropriate methods. Small tests using mixtures of the ballast water containing deactivatable biocide with the neutralizing agent added may be prepared and tested with certified innoculants to determine the optimum amount of neutralizing agent. For glutaraldehyde, there are kits that can be used to determine the concentration. For example, the Hach P.N. 25872-00 kit can be used to determine the concentration of glutaraldehyde in water in the range of 0.5 to 4000 ppm.

The extent of deactivation of the deactivatable biocide in the ballast water is in general sufficient to meet the local regulatory requirements at the ballast water discharge site. The extent of deactivation may also be judged by fish toxicity tests and microbial growth tests. In fish toxicity tests the ballast water containing deactivatable biocide with neutralizing agent added should show no significant toxicity within 1 hour, preferably within 6 hours, more preferably within 24 hours, and most preferably within 96 hours.

In microbial growth tests the ballast water containing deactivatable biocide with neutralizing agent added should support visible growth of microorganisms when placed in contact with a rapidly biodegradable substance within 10 days, preferably within 5 days, and most preferably within 3 days. To perform this test, after the ballast water containing deactivatable biocide has been treated with an effective amount of neutralizing agent to deactivate the biocide, the ballast water is exposed to a certified inoculum, growth media, and rapidly biodegradable product under ambient conditions. For this testing the rapidly biodegradable substance may be a hydrocarbonaceous product. Visible growth of microorganisms is said to occur when the NTU value increases by two units from measurements made before and after the inoculant is introduced into the sample. Ambient conditions mean a temperature between 10° C. and 40° C. and a pH between 6 and 8.5.

According to the present invention, a vessel or ship with a ballast water system may be used to transport products produced using a Fischer-Tropsch process.

As described previously, deactivatable biocides are mixed with ballast water to inhibit the transfer of one or more life forms from one location to another. The deactivatable biocides to be used on such vessels may be provided by producing them at the same Fischer-Tropsch facility used to produce the Fischer-Tropsch products to be carried as cargo.

Fischer Tropsch processes convert natural gas, which is mostly methane, to synthesis gas, or syngas, which is a mixture of carbon monoxide and hydrogen. Catalysts and conditions for performing Fischer-Tropsch synthesis are well known to those of skill in the art, and are described, for example, in EP 0 921 184 A1. In the Fischer-Tropsch synthesis process, liquid and gaseous hydrocarbons are formed by contacting a synthesis gas (syngas) comprising a mixture of $H_2$ and CO with a Fischer-Tropsch catalyst under suitable temperature and pressure reactive conditions. The Fischer-Tropsch reaction is typically conducted at temperatures of from about 300° to 700° F. (149° to 371° C.), preferably from about 400° to 550° F. (204° to 228° C.); pressures of from about 10 to 600 psia, (0.7 to 41 bars), preferably 30 to 300 psia, (2 to 21 bars) and catalyst space velocities of from about 100 to 10,000 cc/g/hr., preferably 300 to 3,000 cc/g/hr.

The products may range from $C_1$ to $C_{200+}$ with a majority in the $C_5$ to $C_{100+}$ range, and the products may be distributed in one or more product fractions. The reaction can be conducted in a variety of reactor types, for example, fixed bed reactors containing one or more catalyst beds; slurry reactors; fluidized bed reactors; and a combination of different type reactors. Such reaction processes and reactors are well known and documented in the literature.

Slurry Fischer-Tropsch processes, which is a preferred process in the practice of the invention, utilize superior heat (and mass) transfer characteristics for the strongly exothermic synthesis reaction and are able to produce relatively high molecular weight, paraffinic hydrocarbons when using a cobalt catalyst. In a slurry process, a syngas comprising a mixture of $H_2$ and CO is bubbled up as a third phase through a slurry in a reactor which comprises a particulate Fischer-Tropsch type hydrocarbon synthesis catalyst dispersed and suspended in a slurry liquid comprising hydrocarbon products of the synthesis reaction which are liquid at the reaction conditions. The mole ratio of the hydrogen to the carbon monoxide may broadly range from about 0.5 to 4, but is more typically within the range of from about 0.7 to 2.75 and preferably from about 0.7 to 2.5. A particularly preferred Fischer-Tropsch process is taught in EP 0609079, incorporated herein by reference in its entirety.

Suitable Fischer-Tropsch catalysts comprise one or more Group VIII catalytic metals such as Fe, Ni, Co, Ru and Re. Additionally, a suitable catalyst may contain a promoter. Thus, a preferred Fischer-Tropsch catalyst comprises effective amounts of cobalt and one or more of Re, Ru, Pt, Fe, Ni, Th, Zr, Hf, U, Mg and La on a suitable inorganic support material, preferably one which comprises one or more refractory metal oxides. In general, the amount of cobalt present in the catalyst is between about 1 and about 50 weight percent of the total catalyst composition. The catalysts can also contain basic oxide promoters such as $ThO_2$, $La_2O_3$, MgO, and $TiO_2$, promoters such as $ZrO_2$, noble metals (Pt, Pd, Ru, Rh, Os, Ir), coinage metals (Cu, Ag, Au), and other transition metals such as Fe, Mn, Ni, and Re. Support materials including alumina, silica, magnesia and titania or mixtures thereof may be used. Preferred supports for cobalt containing catalysts comprise titania. Useful catalysts and their preparation are known and illustrative, but non-limiting examples may be found, for example, in U.S. Pat. No. 4,568,663.

The products from Fischer-Tropsch reactions performed in slurry bed reactors generally include a light reaction product and a waxy reaction product. The light reaction product (i.e. the condensate fraction) includes hydrocarbons boiling below about 700° F. (e.g., tail gases through middle distillates), largely in the $C_5$–$C_{20}$ range, with decreasing amounts up to about $C_{30}$. The waxy reaction product (i.e., the wax fraction) includes hydrocarbons boiling above 600° F. (e.g., vacuum gas oil through heavy paraffins), largely in the $C_{20}$+ range, with decreasing amounts down to $C_{10}$. Both the light reaction product and the waxy product are substantially paraffinic. The products generally comprise greater than 70% normal paraffins, and often greater than 80% normal paraffins. The light reaction product comprises paraffinic products with a significant proportion of alcohols and olefins. In some cases, the light reaction product may comprise as much as 50%, and even higher, alcohols and olefins. In the Fischer Tropsch process, the desired Fischer Tropsch products typically will be isolated by distillation.

The product from the Fischer-Tropsch process may be further processed using, for example, hydrocracking, hydroisomerization, and hydrotreating. Such processes crack the larger synthesized molecules into fuel range and lube range molecules with more desirable boiling points, pour points, and viscosity index properties. Such processes may also saturate oxygenates and olefins to meet the particular needs of a refinery. These processes are well known in the art and do not require further description here.

A preferred Fischer-Tropsch product of a Fischer Tropsch process is a Fischer Tropsch derived liquid product and a preferred product of a Fischer Tropsch process has a branching index of less than five, preferably less than four, more preferably less than three. Fischer-Tropsch (FT) derived products include, for example, Fischer-Tropsch naphtha, Fischer-Tropsch jet fuel, Fischer-Tropsch diesel fuel, Fischer-Tropsch solvent, Fischer-Tropsch lube base stock, Fischer-Tropsch lube base oil, Fischer-Tropsch lube base stock feedstock, and mixtures thereof.

According to the present invention, products from a Fischer Tropsch process may be used as deactivatable biocides in the ballast water of a vessel. The Fischer-Tropsch process may provide products that may be isolated and used directly as deactivatable biocides and products that may be isolated and converted into deactivatable biocides by chemical processes well know to those of skill in the art, including for example, oxidation, dehydration, and/or dehydrogenation. The deactivatable biocides prepared from a Fischer Tropsch process are herein identified as "Fischer Tropsch derived deactivatable biocides." Fischer Tropsch products that may be used to provide Fischer Tropsch derived deactivatable biocides include, for example, oxygenates (including alcohols, aldehydes, and carboxylic acids), olefins, alkynes, and mixtures thereof.

Olefins and oxygenates may be derived from light Fischer Tropsch products. In addition, olefins may be formed, for example, by a thermal cracking process performed on heavy Fischer Tropsch products. Furthermore, oxygenates may be generated as a component of the waste-water generated as part of the Fischer-Tropsch process.

By way of example, the olefins and oxygenates derived from a Fischer Tropsch process may be used to provide aldehydes and alkynes by chemical processes which include oxidation and/or dehydrogenation. One of skill in the art would readily be able to devise methods to generate and isolate olefins and oxygenates from a Fischer-Tropsch process and convert these olefins and oxygenates to aldehydes and alkynes. Alternatively, waste-water generated in the Fischer-Tropsch process may contain a variety of oxygenated hydrocarbons. These oxygenated hydrocarbons may also be used directly or used to generate aldehydes.

Accordingly, a Fischer Tropsch process may be used to generate Fischer Tropsch derived deactivatable biocides for use in ballast water on a vessel as well as Fischer Tropsch derived liquid products to be transported in the cargo tank of such a vessel. Deriving the deactivatable biocide from the Fischer Tropsch process serves several benefits. It removes olefins and oxygenates from the Fischer Tropsch feedstock reducing the amount of potential catalyst poisons in the stream. Furthermore, when a single entity is both shipping the Fischer Tropsch derived liquid products and operating a Fischer-Tropsch facility, Fischer-Tropsch-derived biocides do not have to be purchased from a third party to be used in ballast water.

According to the present invention, Fischer-Tropsch-derived deactivatable biocides may be used in a method of limiting the transfer of one or more life forms from one location to another location via ballast water on a vessel having a ballast water tank. Fischer Tropsch derived liquid products and one or more Fischer-Tropsch-derived deactivatable biocides are synthesized from a Fischer-Tropsch synthesis process. While at a first location, one or more of the Fischer Tropsch derived liquid products are added to the cargo tank on the vessel. Also while at the first location, one or more of the Fischer-Tropsch-derived biocides are added to the ballast water tank and/or a biocide storage area on the vessel. The Fischer-Tropsch derived liquid product or products are delivered to a second location. Ballast water from the second location and an effective amount of the deactivatable biocide are mixed in the ballast water tank. Prior to discharging the ballast water, an effective amount of a neutralizing agent is added to the ballast water to deactivate the biocide. At least a portion of the ballast water is then discharged at the first location or at a third location.

In this method, the effective amount of the deactivatable biocide mixed with the ballast water meets one or both of the following tests: (1) an amount effective to resist visible growth of microorganisms for at least 10 days under ambient conditions when exposed to a certified inoculant; and (2) an amount effective to kill 50% of a predetermined life form within 96 hours.

The present invention also relates to a method of disposing of ballast water that contains a deactivatable biocide. A vessel is provided that has ballast water from a first location. The ballast water contains a deactivatable biocide. An effective amount of a neutralizing agent is added to the ballast water to deactivate the biocide. The ballast water is then discharged from the vessel at a second location. After the biocide is effectively deactivated, the ballast water supports growth of microbial organisms in less than 10 days under ambient conditions when exposed to a certified inoculum, growth media, and a hydrocarbonaceous product. Preferably, the ballast water containing deactivated biocide will support growth of microbial organisms in less than 5 days. Deactivation of the biocide minimizes environmental damage when ballast water is introduced into the environment.

The present invention further relates to a method of inhibiting the growth and reproduction of microorganisms in ballast water used in any vessel. In this method ballast water is provided from a first natural environment for use in the ballast water system of the vessel. To the ballast water is added an effective amount of a deactivatable biocide. An effective amount of biocide is as described previously.

In this method, an effective amount of a neutralizing agent may be added to deactivate the biocide before or upon discharge of the ballast water. After the biocide is effectively deactivated, the ballast water may be discharged into a second natural environment.

The present invention additionally relates to a method of limiting the transfer of one or more life forms from a first location to a second location via ballast water aboard a vessel having a ballast water tank. Ballast water from the first location is mixed with an effective amount of a deactivatable biocide in the ballast tank. Prior to the time the ballast water is discharged, an effective amount of a neutralizing agent is contacted with the ballast water to deactivate the biocide. At least a portion of the ballast water is then discharged at the second location.

In this method, the effective amount of the deactivatable biocide mixed with the ballast water meets one or both of the following tests: (1) an amount effective to resist visible growth of microorganisms for at least 10 days under ambient conditions when exposed to a certified inoculant; and (2) an amount effective to kill 50% of a predetermined life form within 96 hours.

The present invention may also be used in conjunction with other methods of limiting the transfer of life forms through ballast water such as, for example, ballast water exchange, irradiation with ultraviolet (UV) light, filtering of ballast water, and applying heat to the ballast water. The effective amount of deactivatable biocide used in conjunction with other conventional methods is typically less than that used when the deactivatable biocide is used alone. Furthermore, when a deactivatable biocide is used in conjunction with a conventional method, it is typically more effective in preventing the transfer of life forms than the conventional method alone. Therefore, using deactivatable biocides in conjunction with conventional methods may be a more effective and economical method of preventing the transfer of life forms.

In one preferred method, ballast water exchange and deactivatable biocides are both used to limit the transfer of one or more life forms from a beginning location to final location via ballast water. Ballast water from the beginning location is added to a ballast water tank of a vessel. A portion of the water from the beginning location is discharged at an intennediate location. This intermediate location is typically in "mid ocean" (i.e., at least 200 nautical miles from shore), but any location other than the beginning location may be an intermediate location. An effective amount of a deactivatable biocide is added to the remainder of the ballast water from the beginning location. The amount of biocide used is generally less than would be required for a full tank of ballast water. Water from the intermediate location is added to the ballast water tank and, prior to the time the ballast water is discharged, an effective amount of a neutralizing agent is contacted with the ballast water to deactivate the biocide. At least a portion of the ballast water is then discharged at the final location.

EXAMPLES

The invention will be further explained by the following illustrative examples that are intended to be non-limiting.

Example 1

Preparation of Diesel Fuel Samples

A Fischer Tropsch product was generated by reacting synthesis gas over an iron-containing catalyst. The product was separated into a diesel boiling range product (A) and a wax. The diesel product (A) was hydrotreated to remove oxygenates and saturate olefins. The wax was hydrocracked over a sulfided catalyst consisting of amorphous silica-alumina, alumina, tungsten and nickel. A second diesel product (B) was recovered from the effluent of the hydrocracker. The two diesel products were blended in the proportion of 82% B and 18% A by weight. Properties of the Fischer Tropsch (FT) diesel fuel blend are shown in Table 1 along with the ASTM D975 specifications.

TABLE I

Properties of FT Diesel Fuel

| Tests | ASTM D975 Specifications | Fischer-Tropsch Diesel |
|---|---|---|
| Density, 15° C. |  | 0.7695 |
| Sulfur, ppm | 0.05 (% mass max.) | <6 |
| Nitrogen, ng/l |  | 0.69 |
| Cetane Index ASTM D976 | 40 (min.) | 76 |
| Normal Paraffins, wt % |  | 17.24 |
| Non Normal Paraffins, wt % |  | 82.76 |
| Distillation D86, ° F. |  | 333 |
| 10% |  | 371 |
| 50% |  | 478 |
| 90% | 540, 640 (min.), (max.) | 631 |
| 95% |  | 653 |
| EP |  | 670 |

Samples of conventional diesel fuel (C) and California Alternate Low Aromatics Diesel Fuel (ALAD) were also obtained. Properties of these two are shown below in Table II.

TABLE II

Properties of Commercial Diesel Fuels

| Diesel Type: | C | ALAD |
|---|---|---|
| Density @ 15° C., g/mL | 0.8551 | 0.8418 |
| Sulfur, ppm | 4190 | 24 |
| Nitrogen, ppm | 296 | <1 |
| Cetane Index (D 976) | 46.4 | 55.0 |
| D 86 Distillation, ° F. |  |  |
| Start | 348 | 366 |
| 5% | 385 | 448 |
| 10% | 404 | 479 |
| 30% | 470 | 535 |
| 50% | 520 | 566 |
| 70% | 568 | 593 |
| 90% | 634 | 632 |
| 95% | 661 | 652 |
| End Point | 685 | 671 |
| Recovery, % | 98.6 | 98.4 |

Both commercial diesel fuels contain significantly more aromatics than the Fischer-Tropsch diesel fuel, with sample C, the conventional diesel fuel, containing the most. The ALAD sample contains low levels of nitrogen and sulfur.

Example 2

Certification of the Inoculum for Determining the Effectiveness of Biocide Neutralization The purpose of this example was to develop a certified inoculum that can be used to determine the activity of biocides in ballast water and the effectiveness of neutralizing agents on the biocides.

Inoculum Development: The original alkane degrading culture was produced by growing microorganisms from a variety of sources including soils and water known to be contaminated with crude oil and petroleum products. A few micrograms of each source material were added to the minimal medium described below using Fischer-Tropsch diesel as the carbon source. After substantial growth was observed, organisms were removed from the suspension by pipet and added to fresh minimal medium containing Fischer-Tropsch diesel as the carbon source. This source of organisms was used for subsequent experiments. $n\text{-}C_{16}$ could also be used as a carbon source for developing the inoculum.

To determine if the inoculum and other factors of the test, such as growth medium, are suitable for use in determining the speed of biodegradation, $n\text{-}C_{16}$ was obtained from Aldrich Chemical company, and used as a standard hydrocarbon representative of rapidly biodegradable hydrocarbonaceous products.

Growth Media: A standard minimal media containing only inorganic nutrients required for bacterial growth was used. The medium used to supply inorganic micronutrients to the growing culture of alkane degrading organisms consists of 0.1 g/L $MgSO_4 \cdot 7H_2O$, 0.5 g/L $NaNO_3$, 0.02 milli-Moles $FeSO_4$ and 0.63 g/L $K_2HPO_4$ and 0.19 g/L $KH_2PO_4$ to achieve a pH of 7 to 7.3.

Test Conditions: 90 ml of media and 10 ml of the product to be tested (n-C16) were added to 250 ml flasks. 100 µl of the bacterial inoculum was added to each flask. After inoculation, the flasks were placed on a shaker-table (135 rpm) at room temperature in contact with air and observed daily.

The $n\text{-}C_{16}$ showed visual growth of microorganisms at three days in the water phase. Visual growth of microorganisms with $n\text{-}C_{16}$ under these test conditions at less than 4 days demonstrates that the inoculum is certified for determining the speed of biodegradation in this application, and that other factors in the experiment are suitable for this application.

The visual formation of microorganisms can also be measured quantitatively by measuring the turbidity. Turbidity is generally measured by using a turbidity meter, such as a Hach Co. Model 2100 P Turbidimeter. A turbidity meter is a nephelometer that consists of a light source that illuminates a water/lube base oil sample and a photoelectric cell that measures the intensity of light scattered at a 90° angle by the particles in the sample. A transmitted light detector also receives light that passes through the sample. The signal output (units in nephelometric turbidity units or NTUs) of the turbidimeter is a ratio of the two detectors. Meters can measure turbidity over a wide range from 0 to 1000 NTUs. The instrument must meet US-EPA design criteria as specified in US-EPA method 180.1.

Typical lube base oils measured at 75° F. have ranges from 0–20 NTUs. Commercial Poly Alph Olefins (PAOs) tend to have NTUs between 0–1.

When the appearance of the oils is examined (in simulation of a customer's opinion) the following relates the value of the NTU and the appearance:

| NTU Value | Appearance |
|---|---|
| 20 | Cloudy |
| 2–5 noticeable haze | Possibly acceptable, but |
| 0.5–2 | Clear and bright |

References:

drinking water must be <1.0 recreational water must be <5.0

The visual formation of microorganisms is said to occur when the NTU units from measurements made before the microorganisms were introduced into the sample.

Example 3

Test for Rapidly Biodegradable Hydrocarbonaceous Products

The following examples identify Rapidly Biodegradable Hydrocarbonaceous Products.

Test Conditions: 90 ml of growth media and 10 ml of the product to be tested were added to 250 ml flasks. 100 µl of the bacterial inoculum was added to each flask except for the sterile controls.

After inoculation, the flasks were place on a shaker-table (135 rpm) at room temperature in contact with air and observed daily. The sterile control showed no growth or discoloration.

The following Table III summarizes the appearance of visual growth in the three products tested: FT diesel fuel, ALAD Diesel, and conventional diesel.

TABLE III

Appearance of Visual Growth

| Day | FT Diesel Fuel | ALAD Diesel | Conventional Diesel |
|---|---|---|---|
| 0 | − | − | − |
| 2 | − | − | − |
| 3 | + | + | − |
| 4 | + | + | − |
| 5 | + | + | − |
| 6 | + | + | − |
| 7 | + | + | − |
| 8 | + | + | − |

− No Growth
+ Growth (White Unless Otherwise Indicated)

Growth under ten days is representative of a product that is rapidly biodegradable because storage of products for ten days is common, and formation of a visible deposit is not acceptable. Both the FT and the ALAD samples were rapidly biodegradable under these standards while the conventional diesel fuel was not.

Example 4

Evaluation of Biocides

The ability of biocides to inhibit growth on a FT diesel and a low aromatics diesel fuel from Example 1 was investigated.

Test Conditions: 90 ml of growth media and 10 ml of either FT diesel or low sulfur (ALAD) diesel was added to 250 ml flasks. 10 µl of the bacterial inoculum was added to each flask except for the sterile controls. In addition to the 2 alkynes, glutaraldehyde (glutaric dialdehyde 50%), was tested. The following summarizes the test conditions:

Sterile control (media boiled prior to adding FT or ALAD, not inoculated)

Inoculated control (no inhibitor)

100 ppm inhibitor (on a total test volume basis or 1000 ppm in diesel)

1% inhibitor (on a total test volume basis or 10% in diesel).

Three inhibitors were evaluated:

G—glutaraldehyde (glutaric dialdehyde 50%)

H—1-hexyne

P—Propargyl alcohol

After inoculation, the flasks were place on a shaker-table (135 rpm) at room temperature and observed daily.

The following Table IV summarizes the test results obtained using Fischer-Tropsch diesel fuel.

TABLE IV

Test Results on Fischer-Tropsch Diesel Fuel

| Day | Sterile Control | No Biocide | FT Diesel + 100 pm G | FT Diesel + 1 Wt % G | FT Diesel + 100 ppm P | Ft Diesel + 1 Wt % P | FT Diesel + 100 ppm H | FT Diesel + 1 Wt % H |
|---|---|---|---|---|---|---|---|---|
| 0 | − | − | − | − | − | − | − | − |
| 1 | − | − | − | − | − | − | − | − |
| 5 | − | + | − | − | − | − | + | − |
| 7 | − | + | − | − | + | − | + | − |
| 8 | − | + | − | − | + | − | + | − |
| 19 | − | + | + | − | + | − | + | − |

− No Growth
+ Growth (White Unless Otherwise Indicated)

These results demonstrate that all three biocides were effective, with glutaraldehyde being effective at a lower concentration. An effective amount of a biocide is the amount that inhibits microbial growth in a rapidly biodegradable hydrocarbonaceous product for 10 days. As can be seen, these concentrations can vary from less than 100 ppm to about 1 wt %. A suitable range would be 25 ppm to 1 wt %, except where the biocide is a conventional petroleum hydrocarbonaceous product. In this case, the suitable range is between 10 and 90 wt %, preferably 25 to 75 wt %, most preferably about a 50—50 mixture.obtained using ALAD diesel fuel.

The following Table V summarizes the test results

TABLE V

Test Results on ALAD Diesel Fuel

| Day | LA Diesel Fuel | LA Diesel + 100 ppm G | LA Diesel + 1 Wt % G | LA Diesel + 100 ppm H | LA Diesel + 1 Wt % H | LA Diesel + 100 ppm P | LA Diesel + 1 Wt % P |
|---|---|---|---|---|---|---|---|
| 0 | − | − | − | − | − | − | − |
| 1 | − | − | − | − | − | − | − |
| 5 | + | − | − | + | − | + Yellow | − |
| 7 | + | − | − | + | − | + Yellow | − |
| 8 | + | − | − | + | − | + Yellow | − |
| 19 | + | − | − | + | − | + Yellow | − |

− No Growth
+ Growth (White Unless Otherwise Indicated)

These results show that all three biocides were effective, with glutaraldehyde being effective at a lower concentration.

Example 5

Test of Nutrients

The results in Example 4 suggested that the alkynes inhibited growth on FT. A test was conducted to evaluate whether the inhibition was specific for substrates that required oxygenase activity or a general inhibitor of bacterial growth. In this test, growth on a microbial media containing easily degradable organics (sugar, yeast extract) was evaluated in the presence of FT with 1% of each of the inhibitors. 400 ml of media containing 1000 ppm microbial growth substrate YDP was split between 4 flask. 10 ml FT was added to each flask. 3 of the flask received one of the inhibitors. They were inoculated with 100 $\mu$l from the FT inoculated control flask of Experiment 3. All three of the compounds tested inhibit growth on a rich media containing sugars and yeast extract. This suggests that the mode of inhibition is more general than only inactivating monooxygenase enzymes.

Example 6

Partition of the Biocide

This example demonstrates that the biocides are for the most part partitioned in the water phase. The rapidly biodegradable hydrocarbonaceous product was placed in contact with water that contains an effective level of biocide (e.g. 1 wt %). Subsequently, the rapidly biodegradable hydrocarbonaceous product was removed and replaced with a fresh sample of rapidly biodegradable hydrocarbonaceous product. Microbial growth was still inhibited (no growth after 16 days) showing that the biocide remains at an effective concentration in the water.

Example 7

Equivalence of n-C16 and Fischer Tropsch Diesel Fuel as Rapidly Biodegradable Hydrocarbonaceous Products To demonstrate the equivalence of n-C16 and the Fischer Tropsch diesel fuel, 90 ml of media and 10 ml of either FT diesel or n-C16 was added to 250 ml flasks. 10 $\mu$l of the bacterial inoculum was added to each flask. Both showed no growth at 2 days, but at the next observation at 6 days, both showed growth. The onset of growth in both materials at the same time indicates that they have an equivalent onset of microbial growth and can be used interchangeably as rapidly biodegradable hydrocarbonaceous products

Example 8

Neutralization of Biocides—$H_2O_2$ and $NH_4Cl$

This example demonstrates that $H_2O_2$ and $NH_4Cl$ are not effective in neutralizing biocides. In this experiment, minimal medium containing 1, 10 or 100 ppm of glutaraldehyde was mixed with a five times molar excess of $H_2O_2$ or $NH_4Cl$. Hydrocarbonaceous product and bacteria were then added to the mixture. While microbial growth was observed after 5 days in control samples containing no glutaraldehyde, no growth was observed after 14 days in samples containing glutaraldehyde and $H_2O_2$ or $NH_4Cl$ demonstrating that these species were ineffective in neutralizing the glutaraldehyde. Presumably, the $H_2O_2$ remained toxic, and the $NH_4Cl$ did not form a complex with the glutaraldehyde.

Example 9

Neutralization of Biocides with Monoethanolamine

This example demonstrates that amines and aminoalcohols can be used to neutralize biocides. The optimum amount of neutralizing agent to biocide is approximately 1 mole per 1 mole. If excess neutralizing agent is added, it too can act as a biocide because it is toxic, although much less so than the biocide itself. If a large amount of biocide is added (100 ppm or more of glutaraldehyde), the amount of amine added should be fairly close to a 1:1 molar ratio to avoid toxicity problems from the neutralizing amine.

In all experiments, a 10:1 ratio of minimal media to Fischer-Tropsch diesel fuel were prepared and evaluated in 250 ml flasks. To the flasks, various levels of glutaraldehyde (G) and monoethanolamine (MEA) were added.

|  | 5X MEA | 2X MEA | 1X MEA | no MEA |
|---|---|---|---|---|
| 100 ppm G | X | X | X | X |
| 10 ppm G | X | X | X | X |
| 1 ppm G | X | X | X | X |

Then, 10 $\mu$l of the bacterial inoculum was added to each flask.

In addition to these experiments, several controls were run without Glutaraldehyde as follows:

1 ppm MEA control
10 ppm MEA control
100 ppm MEA control
500 ppm MEA control
no G/no MEA control The results of these experiments are shown below in Table VI.

TABLE VI

Neutralization of Biocides with MEA.

| Time (days) | 0 | 1 | 2 | 3 | 7 | 9 | 14 |
|---|---|---|---|---|---|---|---|
| 100 ppm G + 5X MEA | − | − | − | − | − | − | − |
| + 2X MEA | − | − | − | − | − | − | − |
| + 1X MEA | − | − | − | − | + | + | + |
| no MEA | − | − | − | − | − | − | − |
| 10 ppm G + 5X MEA | − | − | − | − | + | + | + |
| + 2X MEA | − | − | − | + | + | + | + |
| + 1X MEA | − | − | − | − | + | + | + |
| no MEA | − | − | − | − | − | − | − |
| 1 ppm G + 5X MEA | − | − | − | − | + | + | + |
| + 2X MEA | − | − | − | + | + | + | + |
| + 1X MEA | − | − | − | − | + | + | + |
| no MEA | − | − | − | − | − | + | + |
| Controls: | | | | | | | |
| 1 ppm MEA | − | − | − | + | + | + | + |
| 10 ppm MEA | − | − | − | + | + | + | + |
| 100 ppm MEA | − | − | − | − | − | − | + |
| 500 ppm MEA | − | − | − | − | − | − | + |
| no G/no MEA | − | − | − | + | + | + | + |

− No Growth
+ Growth

The control results without MEA and without glutaraldehyde shows growth in 3 days as expected. Low levels of MEA in the controls (less than 100 ppm) are not significantly toxic and do not delay the onset of microbial growth. High levels of MEA in the control (100 ppm and higher) are toxic and do delay the onset of microbial growth.

In general, the results demonstrate that adding an equal molar amount of MEA to glutaraldehyde is effective in neutralizing the glutaraldehyde and permitting microbial growth. This is an indication that the biocide has been neutralized, and the water containing the neutralized biocide could safely be discharged or processed in a biological oxidation facility.

The results also show that 1 ppm of glutaraldehyde is moderately effective in delaying the onset of microbial growth—delayed from 3 days to 9 days. 10 ppm is more effective—delayed from 3 days to more than 14 days.

At low levels of glutaraldehyde (below 100 ppm), less than 5 moles MEA to glutaraldehyde are needed to be effective in neutralizing the glutaraldehyde and to yield a water fraction that permits microbial growth, and so by inference is safe to discharge or treat in on-shore facilities. The minimum ratio of MEA to glutaraldehyde is below 1.0 and may be as low as 0.2. However, further routine experiments would be needed to define this lower limit.

At high levels of glutaraldehyde (100 ppm and above), a precise amount of MEA, approximately equal to 1 mole of MEA to glutaraldehyde, is needed to yield a water fraction that permits microbial growth, and so by inference is safe to discharge or treat in on-shore facilities. Excessive amounts of either glutaraldehyde or MEA would yield a water phase that did not permit microbial growth.

Experiment 10

Neutralization of Biocides with Other Nitrogen Compounds

A series of different nitrogen-containing compounds were evaluated as materials to neutralize glutaraldehyde. For these experiments, 10:1 ratio of minimal media to n-$C_{16}$ were prepared, mixed with 10 ppm of glutaraldehyde (G) and evaluated in 250 ml flasks. The different nitrogen-containing compounds evaluated include the following:

Monoethanolamine (MEA)
Diethanolamine (DEA)
Methyldiethanolamine (MDEA)
Diethylamine (DA)
Aniline (A)

Two moles of each of the nitrogen-containing compound to glutaraldehyde were added to the flasks. Then 10 μl of the bacterial inoculum was added to each flask.

The results are shown below in Table VII.

Control samples were also run with the nitrogen-containing compound and without the glutaraldehyde. These control samples permitted an assessment of the toxicity of the nitrogen-containing compound.

TABLE VII

Neutralization of Biocides with Nitrogen Compounds

| Time (days) | 0 | 1 | 2 | 6 | 7 | 9 | 13 | 20 |
|---|---|---|---|---|---|---|---|---|
| With MEA | − | − | − | + | + | + | + | + |
| MEA control | − | − | − | − | + | + | + | + |
| With DEA | − | + | + | + | + | + | + | + |
| DEA control | − | − | − | + | + | + | + | − |
| with MDBA | − | − | − | − | + | + | + | + |
| MDEA control | − | − | − | + | + | + | + | + |
| with diethylamine | − | − | − | + | + | + | + | + |
| Diethylamine control | − | − | − | + | + | + | + | + |
| with aniline | − | − | − | − | − | − | − | − |
| aniline control | − | − | − | − | − | − | − | − |
| Control: no G/no amine | − | − | − | + | + | + | + | + |

− No Growth
+ Growth

These results show that MEA, DEA, MDEA, and diethylamine are all effective in neutralizing 10 ppm of glutaraldehyde. Furthermore, these nitrogen-containing compounds are not excessively toxic themselves and permit microbial growth even in the absence of glutaraldehyde. In contrast, aniline is excessively toxic and does not permit microbial growth in experiments with or without glutaraldehyde.

Experiment 11

Inhibition of Microbial Growth by use of Conventional Petroleum Products

To evaluate the use of conventional petroleum products to inhibit microbial growth a series of blends of the Fischer Tropsch (FT) diesel fuel and the conventional (C) diesel fuel of Experiment 1 were prepared.

For these experiments, 10:1 ratio of minimal media to the mixed feed were prepared, mixed with 10 μl of the bacterial inoculum, and evaluated in 250 ml flasks. The results of these experiments are shown in Table VIII.

TABLE VIII

| Time (Days) | 2 | 3 | 7 | 8 | 10 | 14 | 21 |
|---|---|---|---|---|---|---|---|
| 0.5% C–99.5% FT | − | − | + | + | + | + | + |
| 1% C–99% FT | − | − | + | + | + | + | + |
| 5% C–95% FT | − | − | + | + | + | + | + |
| 10% C–90% C | − | − | + | + | + | + | + |
| 25% C–75% FT | − | − | − | − | − | − | + |
| 50% C–50% FT | − | − | − | − | − | − | − |
| FT with no C | − | − | + | + | + | + | + |
| C with no Fischer-Tropsch | − | − | − | − | − | − | − |

When more than 10% conventional fuel component is mixed with a rapidly biodegradable product, such as a Fischer Tropsch diesel fuel, the resulting blend will no longer be rapidly biodegradable. It can then be safely stored or transported without the use of biocides, or with the use of lower levels of biocides. The blend will of course contain sulfur and other impurities which originate from the conventional fuel component. These can be removed by a number of processes: hydrotreating, hydrocracking, hydroisomerization, extraction, and adsorption. Processing with hydrogen (hydrotreating, hydrocracking and hydroisomerization) are the preferred methods of removing these impurities, with hydrotreating being the most preferred.

Experiment 12

Comparing the Acute Toxicity of Glutaraldehyde and Glutaraldehyde Neutralized with Monoethanolamine (MEA) to Larval Sheepshead Minnow (*Cyprinodon variegatus*)

In a control experiment, the acute toxicity of separate biocide (glutaraldehyde) and neutralizing agent (MEA) was measured in a 96 h static bioassay test (Methods for Measuring the Acute Toxicity of Effluent and Receiving Waters to Freshwater and Marine Organisms, $4^{th}$ edition. EPA/600/4-90/027F Washington, D.C.) conducted at Pacific Eco-Risk Laboratories, Martinez, Calif. The results are summarized in Table IX below.

TABLE IX

Acute Toxicity measured on Larval
Sheepshead Minnow (*Cyprinodon variegatus*)

| Compound | LC-50 (mg/L) | LOEC (mg/L) | NOEC (mg/L) |
|---|---|---|---|
| Glutaraldehyde | 26 | 25 | 13 |
| Monoethanolamine | 1500 | 1700 | 1000 |

LOEC is the Lowest Observable Effect Concentration and is defined as the minimum concentration where mortality is observed for the test species. NOEC is the No Observable Effect Concentration and is defined as the highest concentration tested where no mortality was observed in the test species. LC-50, the concentration that will cause mortality of 50% of the organisms tested within 96 h, is a calculated value based on all observations.

In a second experiment, the toxicity of glutaraldehyde in the presence and absence of MEA was measured and compared. Based on the results of the control experiment above, solutions having the concentrations of glutaraldehyde and MEA listed in Table X below were prepared in the fish bioassay media provided by the testing laboratory. The solutions were mixed for 48 hours prior to the start of the bioassays. The solutions were diluted to perform bioassays at starting glutaraldehyde concentrations of 100, 50, 37.5, 25, and 10.5 mg/L. The results are summarized in Table X.

TABLE X

Acute Toxicity measured on Larval
Sheepshead Minnow (*Cyprinodon variegatus*)

| Glutaraldehyde (mg/L) | MEA (mg/L) | Glutaraldehyde: MEA Molar Ratio | LC50 (mg/L) |
|---|---|---|---|
| 100 | 0 | — | 25 |
| 100 | 62.5 | 1:1 | >100 |
| 100 | 125 | 1:2 | >100 |

The toxicity of glutaraldehyde alone was found to be the same as that determined in the control experiment. Surprisingly no fish mortality was observed at any of the test concentrations where MEA was added. Consequently the LC50 for the neutralized biocide is greater than the maximum concentration tested or 100 mg/L. This is consistent with the observations made on hydrocarbon degrading microorganisms. Thus, ballast water treated by such a technique would have significantly reduced glutaraldehyde toxicity when discharged into the environment or processed in a biological oxidation facility.

While the invention has been described in detail and with reference to specific embodiments thereof, it will be apparent to one skilled in the art that various changes and modifications can be made without departing from the spirit and scope of the invention.

What is claimed is:

1. A method of disposing of ballast water containing a deactivatable biocide, the method comprising the steps of:
   a) providing a vessel having ballast water from a first location, the ballast water containing a deactivatable biocide wherein the deactivatable biocide is an aldehyde or an alkyne;
   b) adding an effective amount of a neutralizing agent to the ballast water to deactivate wherein the neutralizing agent is a nitrogen-containing compound selected from the group consisting of amines, amino acids, amino alcohols, and mixtures thereof when the biocide is an aldehyde or the neutralizing agent is a hydrogenation hydrogenation catalyst and $H_2$ when the biocide is an alkyne; and
   c) discharging the ballast water from the vessel at a second location.

2. The method of claim 1 wherein the biocide is an aldehyde and the neutralizing agent is a nitrogen-containing compound selected from the group consisting of amines, amino acids, amino alcohols, and mixtures thereof.

3. The method of claim 1 wherein the biocide is an alkyne and the neutralizing agent is a hydrogenation catalyst and $H_2$.

4. The method of claim 2 wherein the biocide is glutaraldehyde and the nitrogen-containing compound is selected from the group consisting of monethanolamine, diethanolamine, methyldiethanolamine, and diethylamine.

5. The method of claim 1 wherein after the neutralizing agent is added, the ballast water supports visible growth of microorganisms in less than 10 days when exposed to a certified inoculum, growth media, and rapidly biodegradable hydrocarbonaceous product under ambient conditions.

6. A method of inhibiting growth and reproduction of microorganisms in a ballast water system of a vessel, the method comprising the steps of:
   a) providing ballast water to the ballast water system from a first natural environment;
   b) adding an effective amount of a deactivatable biocide to the ballast water wherein the deactivatable biocide is an aldehyde or an alkyne;
   c) adding an effective amount of a neutralizing agent to the ballast water to deactivate the biocide before or upon discharge of the ballast water wherein the neutralizing agent is a nitrogen-containing compound selected from the group consisting of amines, amino acids, amino alcohols, and mixtures thereof when the biocide is an aldehyde or the neutralizing agent is a hydrogenation catalyst and $H_2$ when the biocide is an alkyne; and
   d) discharging at least a portion of the ballast water into a second natural environment after the biocide has been deactivated.

7. A method of limiting the transfer of one or more life forms from a first location to a second location via ballast water, the method comprising:

a) providing a vessel having a ballast water tank;
b) mixing ballast water from the first location and an effective amount of a deactivatable biocide in the ballast water tank wherein the deactivatable biocide is an aldehyde or an alkyne;
c) contacting an effective amount of a neutralizing agent with the ballast water to deactivate the biocide wherein the neutralizing agent is a nitrogen-containing compound selected from the group consisting of amines, amino acids, amino alcohols, and mixtures thereof when the biocide is an aldehyde or the neutralizing agent is a hydrogenation catalyst and $H_2$ when the biocide is an alkyne; and
d) discharging at least a portion of the ballast water at the second location.

8. The method of claim 7 wherein the amount of the deactivatable biocide mixed with the ballast water in step (b) is an amount effective to resist visible growth of microorganisms for at least 10 days under ambient conditions when exposed to a certified inoculant.

9. The method of claim wherein the amount of the deactivatable biocide mixed with the ballast water in step (b) is an amount effective to kill 50% of a predetermined life form within 96 hours.

10. The method of claim 9 wherein the predetermined life form is selected from the group consisting of zebra mussel, dinoflagellates, and cholera bacteria.

11. The method of claim 7 wherein the biocide is added in an amount of at least 100 ppm.

12. The method of claim 7 wherein the biocide is an aldehyde and the neutralizing agent is a nitrogen-containing compound selected from the group consisting of amines, amino acids, amino alcohols, and mixtures thereof.

13. The method of claim 12 wherein the biocide is glutaraldehyde and the nitrogen-containing compound is selected from the group consisting of monethanolamine, diethanolamine, methyldiethanolamine, and diethylamine.

14. The method of claim 7 wherein after the neutralizing agent is added, the ballast water supports visible growth of microorganisms in less than 10 days when exposed to a certified inoculum, growth media, and rapidly biodegradable hydrocarbonaceous product under ambient conditions.

15. The method of claim 7 wherein the biocide is an alkyne and the neutralizing agent is a hydrogenation catalyst and $H_2$.

16. A method of limiting the transfer of one or more life forms from one location to another location via ballast water, the method comprising:
a) providing a vessel having a ballast water tank and a cargo tank;
b) synthesizing Fischer-Tropsch-derived liquid products and a Fischer-Tropsch derived deactivatable biocide from a Fischer-Tropsch synthesis process;
c) adding, at a first location, one or more of the Fischer-Tropsch-derived liquid products to the cargo tank and the Fischer-Tropsch derived deactivatable biocide to the ballast water tank or to a biocide storage area on the vessel;
d) delivering the one or more Fischer-Tropsch-derived liquid products in the cargo tank to a second location;
e) mixing ballast water from the second location and an effective amount of the deactivatable biocide in the ballast water tank;
f) adding an effective amount of a neutralizing agent to the ballast water to deactivate the biocide; and
g) discharging at least a portion of the ballast water at the first location or a third location.

17. The method of claim 16 wherein the biocide is an alkyne and the neutralizing agent is a hydrogenation catalyst and $H_2$.

18. The method of claim 16 wherein after the neutralizing agent is added, the ballast water supports visible growth of microorganisms in less than 10 days when exposed to a certified inoculum, growth media, and rapidly biodegradable hydrocarbonaceous product under ambient conditions.

19. The method of claim 16 wherein the amount of the deactivatable biocide mixed with the ballast water in step (e) is an amount effective to resist visible growth of microorganisms for at least 10 days under ambient conditions when exposed to a certified inoculant.

20. The method of claim 16 wherein the amount of the deactivatable biocide mixed with the ballast water in step (e) is an amount effective to kill 50% of a predetermined life form within 96 hours.

21. The method of claim 16 wherein the biocide is an aldehyde and the neutralizing agent is a nitrogen-containing compound selected from the group consisting of amines, amino acids, amino alcohols, and mixtures thereof.

22. A method of limiting the transfer of one or more life forms from a beginning location to a final location via ballast water, the method comprising:
a) providing a vessel having a ballast water tank;
b) adding water from the beginning location to the ballast water tank;
c) discharging a portion of the ballast water at an intermediate location wherein the deactivatable biocide is an aldehyde or an alkyne;
d) adding an effective amount of a deactivatable biocide to the remainder of the water from the beginning location;
e) adding water from the intermediate location to the ballast water tank;
f) adding an effective amount of a neutralizing agent to the ballast water to deactivate the biocide wherein the neutralizing agent is a nitrogen-containing compound selected from the group consisting of amines, amino acids, amino alcohols, and mixtures thereof when the biocide is an aldehyde or the neutralizing agent is a hydrogenation catalyst and $H_2$ when the biocide is an alkyne; and
g) discharging at least a portion of the ballast water at the final location.

23. The method of claim 22 wherein the biocide is an alkyne and the neutralizing agent is a hydrogenation catalyst and $H_2$.

24. The method of claim 22 wherein after the neutralizing agent is added, the ballast water supports visible growth of microorganisms in less than 10 days when exposed to a certified inoculum, growth media, and rapidly biodegradable hydrocarbonaceous product under ambient conditions.

25. The method of claim 22 wherein the amount of the deactivatable biocide added to the ballast water in step (d) is an amount effective to resist visible growth of microorganisms for at least 10 days under ambient conditions when exposed to a certified inoculant.

26. The method of claim 22 wherein the amount of the deactivatable biocide added to the ballast water in step (d) is an amount effective to kill 50% of a predetermined life form within 96 hours.

27. The method of claim 22 wherein the biocide is an aldehyde and the neutralizing agent is a nitrogen-containing compound selected from the group consisting of amines, amino acids, amino alcohols, and mixtures thereof.

* * * * *

UNITED STATES PATENT AND TRADEMARK OFFICE
CERTIFICATE OF CORRECTION

PATENT NO. : 6,626,122 B2
DATED : September 30, 2003
INVENTOR(S) : O'Reilly et al.

It is certified that error appears in the above-identified patent and that said Letters Patent is hereby corrected as shown below:

Column 23,
Line 21, please add the number -- 8 -- after the word "claim".

Signed and Sealed this

Tenth Day of August, 2004

JON W. DUDAS
*Acting Director of the United States Patent and Trademark Office*